US010500409B2

(12) United States Patent
Petty et al.

(10) Patent No.: US 10,500,409 B2
(45) Date of Patent: Dec. 10, 2019

(54) SYSTEMS AND METHODS FOR PROVIDING ALTERNATING MAGNETIC FIELD THERAPY

(71) Applicant: KAIO Therapy, LLC, Raleigh, NC (US)

(72) Inventors: Christopher Petty, Cary, NC (US); Lev Zilberter, Morrisville, NC (US); John Popow, Cary, NC (US)

(73) Assignee: KAIO Therapy, LLC, Raleigh, NC (US)

( * ) Notice: Subject to any disclaimer, the term of this patent is extended or adjusted under 35 U.S.C. 154(b) by 83 days.

(21) Appl. No.: 15/058,900

(22) Filed: Mar. 2, 2016

(65) Prior Publication Data

US 2016/0256704 A1 Sep. 8, 2016

Related U.S. Application Data

(60) Provisional application No. 62/127,327, filed on Mar. 3, 2015, provisional application No. 62/127,249, filed on Mar. 2, 2015.

(51) Int. Cl.
*A61N 2/02* (2006.01)
*A61N 2/00* (2006.01)
*A61N 1/40* (2006.01)

(52) U.S. Cl.
CPC ............... *A61N 2/02* (2013.01); *A61N 1/406* (2013.01); *A61N 2/004* (2013.01)

(58) Field of Classification Search
CPC .......... A61N 1/403; A61N 2/00; A61N 2/004; A61N 2/02

(Continued)

(56) References Cited

U.S. PATENT DOCUMENTS 5,203,782 A 4/1993 Gudov et al.
6,124,787 A * 9/2000 Isakov ................ G01D 5/2073 340/442

(Continued)

FOREIGN PATENT DOCUMENTS

CN 2247035 2/1997
CN 1846808 A 10/2006

(Continued)

OTHER PUBLICATIONS

Patent Cooperation Treaty, International Search Report and Written Opinion, International Application No. PCT/US2016/020440 dated May 5, 2016.

(Continued)

*Primary Examiner* — Samuel G Gilbert
(74) *Attorney, Agent, or Firm* — Kilpatrick Townsend & Stockton LLP

(57) ABSTRACT

Examples of systems and methods for providing alternating magnetic field therapy are provided. One example method includes the steps of positioning a target proximate to a first end of an alternating magnetic field (AMF) head, the AMF head comprising an electrical coil and a ferromagnetic core, the electrical coil having a substantially circular cross-section that is substantially centered on a first axis, the AMF head having the first end corresponding to a first end of the coil and a second end corresponding to a second end of the coil; generating and transmitting an alternating current (AC) signal to the AMF head; determining a temperature of the target based on a sensor signal from a temperature sensor; in response to determining the temperature, modifying the AC signal based on a difference between the temperature and a predetermined target temperature.

18 Claims, 17 Drawing Sheets

120

200

110

(58) Field of Classification Search
USPC ............................ 600/9, 10, 13, 14; 607/103
See application file for complete search history.

(56) References Cited

U.S. PATENT DOCUMENTS 6,520,903 B1 2/2003 Yamashiro
6,663,556 B2 12/2003 Barker
7,282,479 B2 10/2007 Ito et al.
7,670,676 B2 3/2010 Horiishi et al.
8,214,053 B2 7/2012 Hirayama et al.
8,246,529 B2 8/2012 Riehl et al.
8,292,879 B2 * 10/2012 Manwaring .......... A61B 18/082 606/27
8,489,201 B2 * 7/2013 Unetich ................. A61N 1/403 606/33
2005/0090735 A1 * 4/2005 Carney .................... A61B 5/01 600/424
2006/0020312 A1 1/2006 Eggers et al.
2006/0265609 A1 * 11/2006 Fung ..................... G06F 1/3203 713/300
2008/0089472 A1 4/2008 Yoon
2008/0249349 A1 10/2008 Vancraeyenest
2008/0281318 A1 11/2008 Herbette et al.
2009/0319010 A1 12/2009 Hirayama et al.
2010/0100092 A1 * 4/2010 Turner ................... A61B 18/18 606/33
2011/0165255 A1 7/2011 Kobayashi et al.
2012/0016174 A1 1/2012 De Taboada et al.
2012/0259154 A1 10/2012 Hong et al.
2012/0283503 A1 11/2012 Ostrovska
2013/0053620 A1 2/2013 Susedik et al.
2014/0243701 A1 8/2014 Southern et al.
2014/0366672 A1 * 12/2014 Urano .................. B25J 15/0009 74/490.01
2015/0119961 A1 4/2015 Kobayashi et al.
2016/0158397 A1 6/2016 Duffield
2016/0317829 A1 11/2016 Hirayama et al.
2016/0317830 A1 11/2016 Hirayama et al.

FOREIGN PATENT DOCUMENTS

CN 100490739 5/2009
DE 103 32 771 A1 3/2005
EP 1 036 574 A1 9/2000
JP 3737054 B2 1/2006
JP 3767820 B2 4/2006
JP 3783811 B2 6/2006
JP 4097580 B2 6/2008
JP 4255466 B2 4/2009
JP 4338961 B2 10/2009
JP 4727363 7/2011
JP 4731185 B2 7/2011
JP 4734006 B2 7/2011
JP 4966575 B2 7/2012
JP 5031979 B2 9/2012
JP 5321772 B2 10/2013
WO 1998/06342 A1 2/1998
WO 2005/089869 A1 9/2005
WO 2011/089472 A1 7/2011
WO 2016025768 2/2016
WO 2016141051 9/2016

OTHER PUBLICATIONS

International Application No. PCT/JP2014/075767, International Search Report and Written Opinion, dated Dec. 16, 2014, 12 pages.
SG Application No. 11201707030Q, Written Opinion, dated Sep. 21, 2018, 8 pages.
EP Application No. 16759407.6, Extended European Search Report, dated Jun. 18, 2018, 7 pages.
Australian Application No. AU2016226262, "First Examination Report", dated Sep. 16, 2019, 4 pages.

* cited by examiner 100
120
121
122
124
126
130
110
115
112
116
114
113

120
200
110

200
120
110

120
110

300
330
310
310
310
310
320

320
320
320
330
310
310
320
320
320

SYSTEMS AND METHODS FOR PROVIDING ALTERNATING MAGNETIC FIELD THERAPY

CROSS-REFERENCE TO RELATED APPLICATIONS

This application claims priority to U.S. Provisional Patent Application No. 62/127,249, entitled "Systems and Methods for Providing Alternating Magnetic Field Therapy," filed Mar. 2, 2015, and to U.S. Provisional Patent Application No. 62/127,327, entitled "Systems and Methods for Providing Alternating Magnetic Field Therapy," filed Mar. 3, 2015, both of which are incorporated by reference in their entirety.

COPYRIGHT NOTIFICATION

A portion of the disclosure of this patent document and its attachments contain material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

FIELD

The present disclosure generally relates to providing alternating magnetic field (AMF) therapy, and more specifically relates to providing AMF therapy to medical patients.

BACKGROUND

Treatment of tumors can be difficult in cancer patients due to the location of the tumors. They are often in locations that are difficult or impossible to reach through conventional surgery. If surgery is possible, it can be difficult to ensure that all portions of the tumor are removed. Remnants of a tumor left in a patient after surgery can result in regrowth of the tumor over time. Instead of surgery, it may be possible to kill tumor cells by heating them. For example, small iron particles can be injected into a tumor and heated using an alternating magnetic field, which can result in tumor cell damage or death.

SUMMARY

Various examples are described for systems and methods for providing alternating magnetic field therapy.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 3A-7 show example ferromagnetic cores for providing AMF therapy;

DETAILED DESCRIPTION

Figure 1:
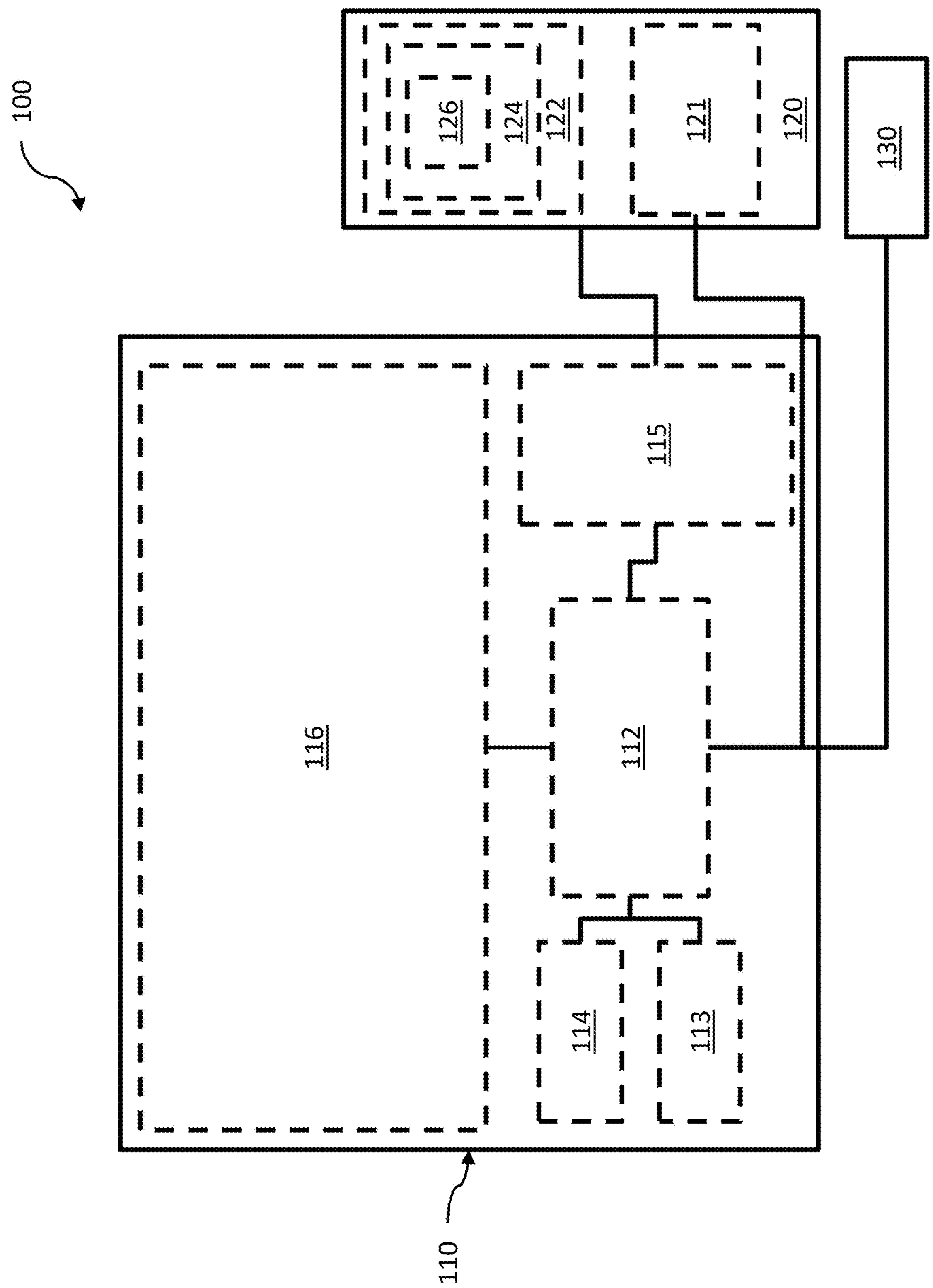
FIG. 1 shows an example system for providing AMF therapy.
Figures 2A, 2B, 2C:
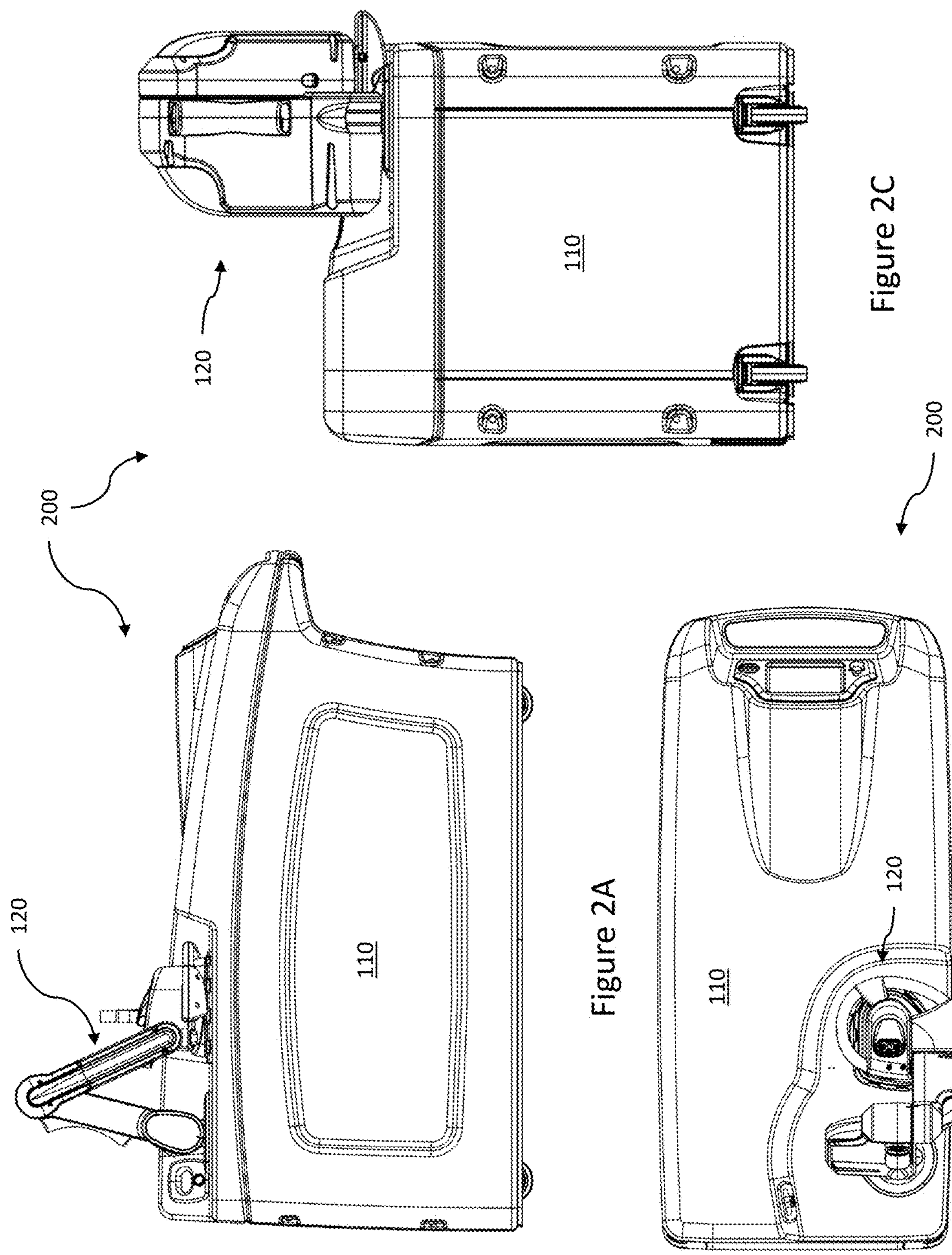
FIGS. 2A-2J show perspective and exploded views of an example system for providing AMF therapy.
Figure 2D:
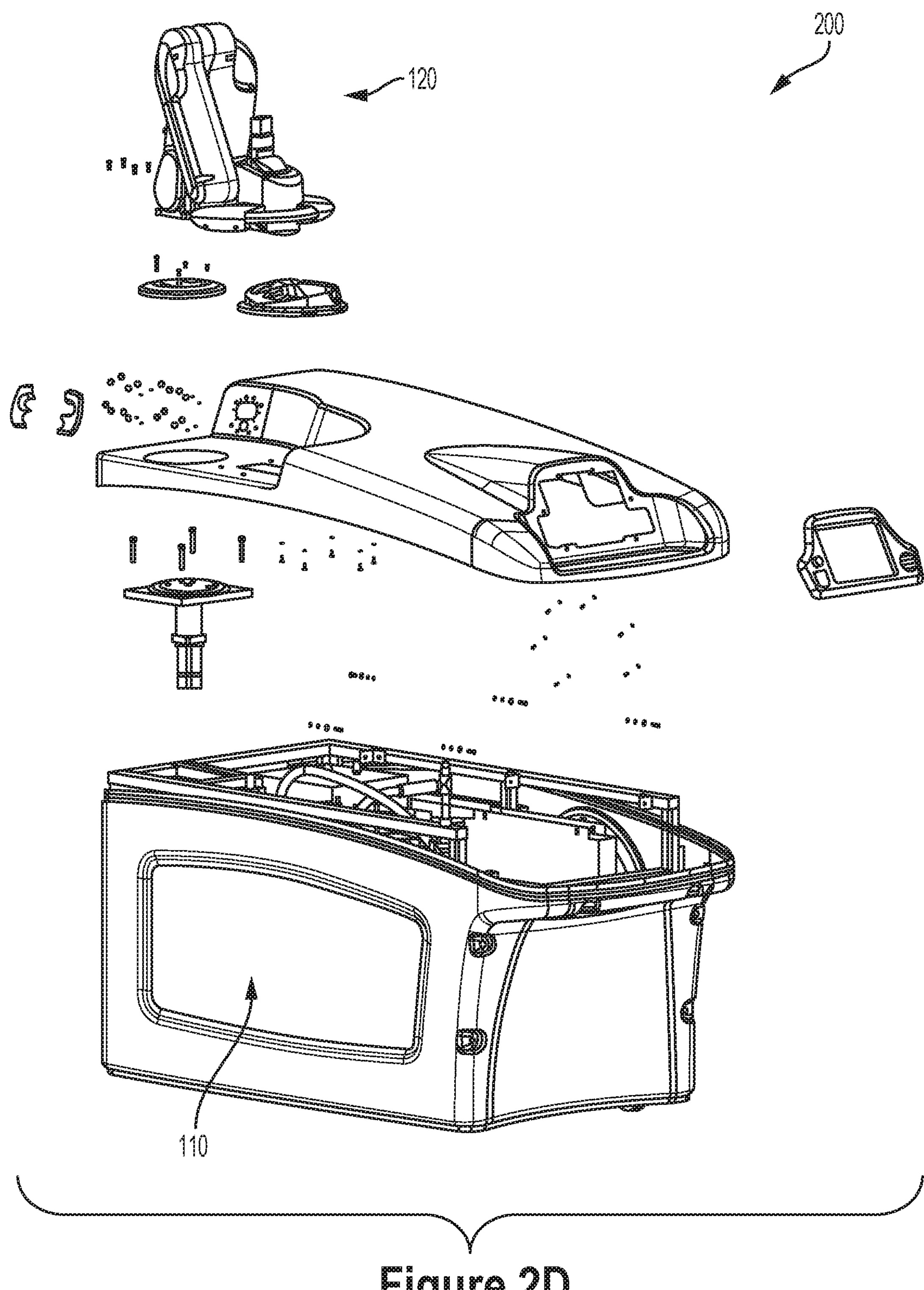
Figure 2E:
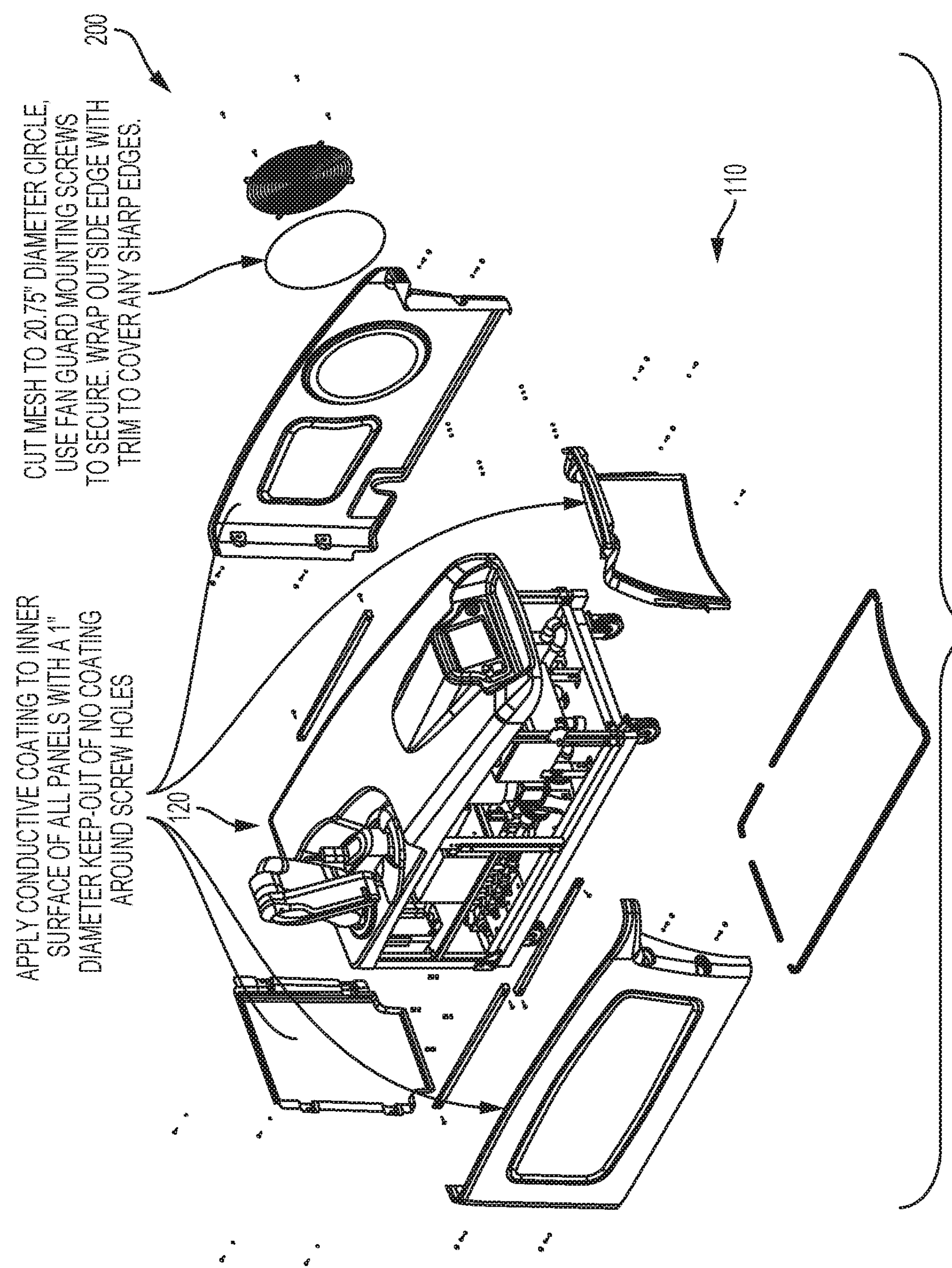
Figure 2G:
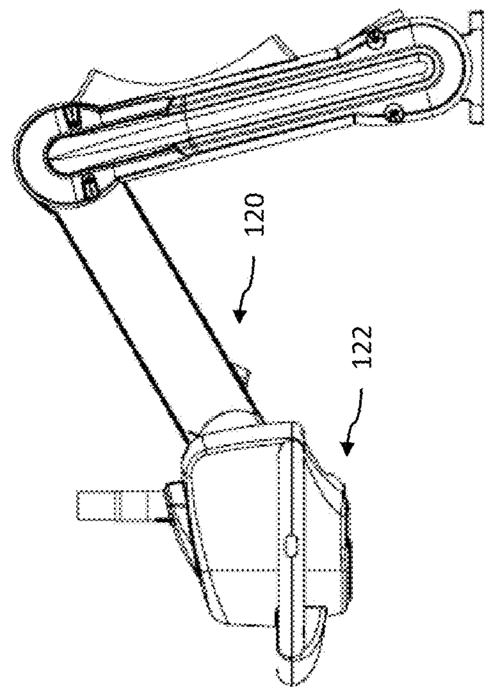
Figure 2I:
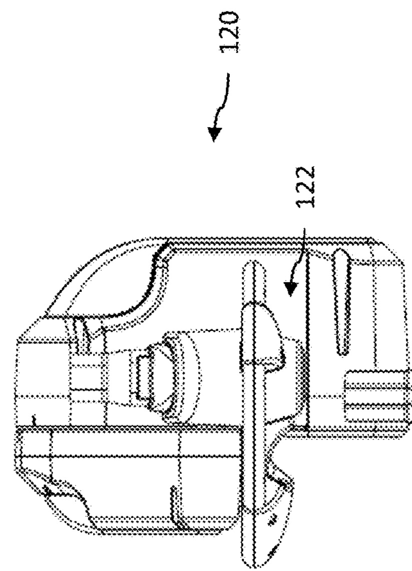
Figure 2F:
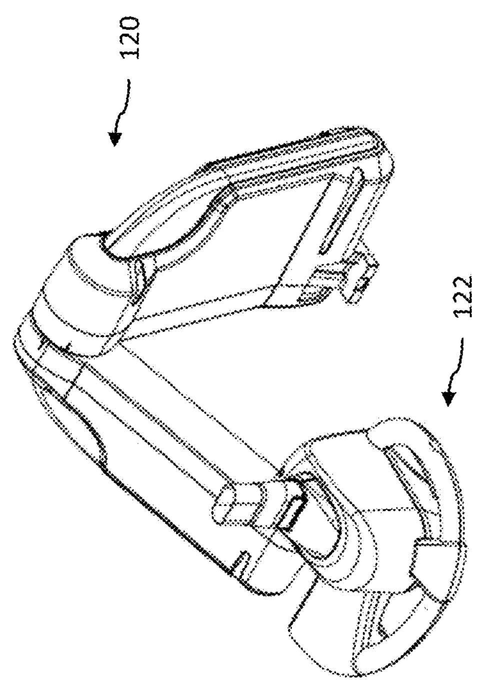
Figure 2H:
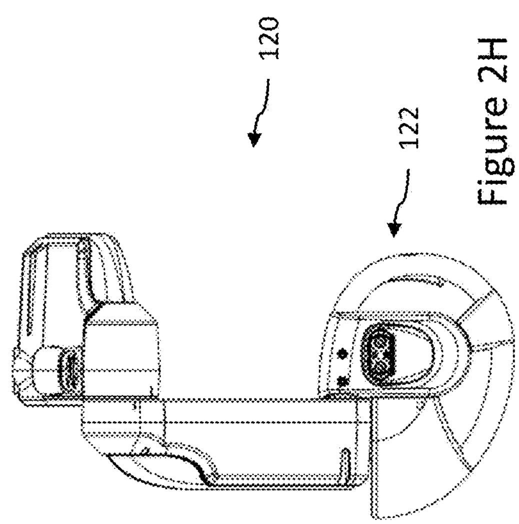
Figure 2J:
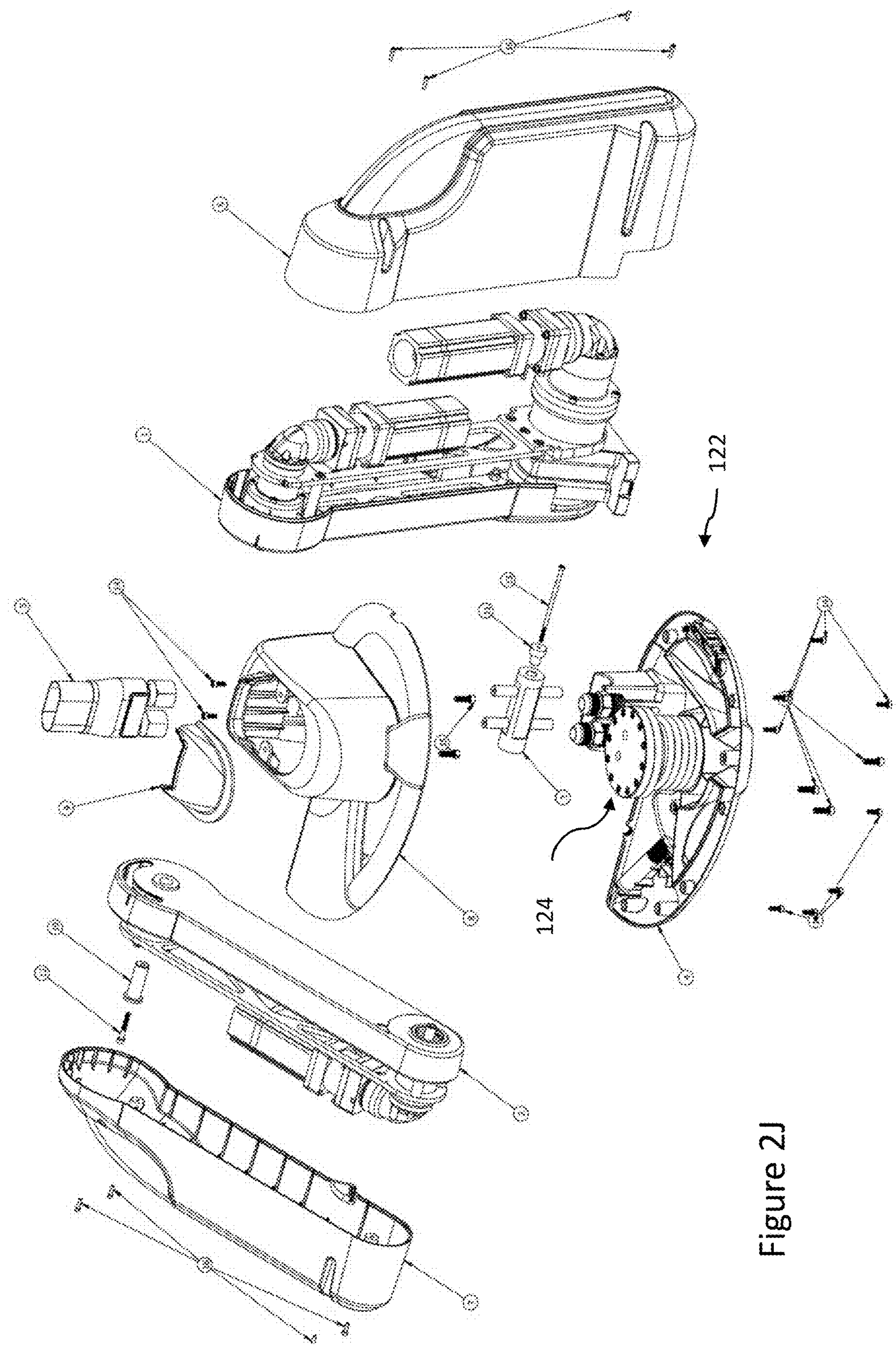

Examples are described herein in the context of systems and methods for providing alternating magnetic field therapy. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Illustrative Example of Providing Alternating Magnetic Field Therapy

In one illustrative example, a patient arrives at her doctor's office for treatment of a tumor on her arm. She is seated and her arm is propped on a flat surface, such as a table. An articulating arm or an AMF system in the room is moved to allow the AMF head on the articulating arm to be positioned over the patient's arm at the location of the tumor. The AMF head is then lowered such that the lower face of the AMF head is positioned about 10 mm above the patient's arm. Prior to this point in the procedure, a number of ferromagnetic nanoparticles were injected into the tumor on her arm. During treatment the ferromagnetic nanoparticles will be subjected to an AMF generated by the AMF head and will heat up.

Once the AMF head has been positioned, an operator, such as the doctor, enters information into the AMF system regarding the therapy to be provided. In this example, the operator specifies a target temperature for the tumor of 46 degrees Celsius to be maintained for 30 minutes and instructs the AMF system to begin the treatment.

In response, the AMF system activates an alternating current (AC) signal generator to transmit an AC current to the AMF head. In this example, the AC signal has a frequency of approximately 106 kilohertz (kHz), though other frequencies may be used. The AC current travels through an electrical coil in the head, within which is positioned a core made of a ferromagnetic material. The AC current travelling through the electrical coil induces an alternating magnetic field through the core, which is projected onto the patient's arm, the tumor, and the ferromagnetic nanoparticles materials within the tumor, which is the ultimate target. In turn, the AMF interacts with the ferromagnetic nanoparticles and the oscillations cause the ferromagnetic nanoparticles to heat up, which in turn heats the surrounding tissue, e.g., the tumor.

As the target tissue heats, the AMF system monitors the temperature of the target tissue with a temperature sensor. In this case, the AMF system uses an infrared camera to capture infrared images of the target. An infrared image is then displayed to the operator, who then selects the region of interest in the image, which is used by the AMF system to identify the relevant portion of the capture images to determine the temperature of the target tissue. In this example, the color data in the image is mapped to corresponding temperature ranges, which are then used to determine the temperature of the tissue.

As the target tissue heats, the AMF system continuously compares the tissue temperature with the target temperature, 46 degrees Celsius in this example. While the tissue temperature is below target temperature, the AMF system commands the AC signal generator to maintains a high AC current level. Over time, as the tissue temperature approaches and reaches the target temperature, the AMF system reduces the power output of the AC signal generator to slow the temperature increase of the target tissue based on the temperature readings from the infrared images, and then to maintain the target temperature, again based on the infrared images. Once the target temperature has been reached, the AMF system maintains the temperature for 30 minutes, and then discontinues the AC signal to terminate the AMF. The operator returns the articulating arm to its standby position and the patient is released from the doctor's office.

This illustrative example is not intended to be in any way limiting, but instead is intended to provide an introduction to the subject matter of the present application. For example, the illustrative example above is described with respect to a smartphone; however, the present application is not limited to such a device, but may be used in any suitable device. Other examples of systems and methods for providing alternating magnetic field therapy are described below.

Referring now to FIG. 1, FIG. 1 shows a block diagram of an example AMF system 100 for providing alternating magnetic field therapy. Different perspective and exploded views of the example AMF system 100 are also shown in FIGS. 2A-2J. The AMF system 100 includes a base unit 110 and an articulating arm unit 120 and one or more thermal sensors 130. The base unit 110 includes a processor 112, a computer-readable medium 113, an AC generator and power supply 115, a cooling system 116, and an operator display 114. The articulating arm 120 has an AMF head 122 having an electrical coil 124 and a ferromagnetic core 126 within the electrical coil 124. The articulating arm 120 also has actuators 121 that enable the position and orientation of the articulating arm 120 and the AMF head 122 to be changed according to commands provided by the processor 112.

The AC generator and power supply 115 is configured to generate an AC signal and provide the AC signal to the AMF head 122 within the articulating arm unit 120. The AMF head 122 can receive the AC signal and, in response, generate, using the electrical coil 124 and ferromagnetic core 126, and project AMF radiation from the AMF head 122 towards a target. In some examples, the target is biological tissue that has been infused with ferromagnetic nanoparticles that can receive the AMF radiation, and in response, heat up, thereby heating the target. In some examples, the ferromagnetic nanoparticles include magnetite coated liposomes (MCL) nanoparticles.

The cooling system 116 is configured to circulate a liquid coolant to cool the AC generator and power supply 115 and may include one or more radiators or fans to allow for cooling of the liquid coolant.

The operator display 114 includes one or more display screens that can display information for the operator. In some examples, the operator display 114 includes a touch-screen display for use by the operator to provide input to the AMF system. In some examples, in addition to, or instead of, the operator display, the base unit 110 may have one or more user manipulatable devices (manipulandum or manipulanda) that the user can employ to interact with the AMF system. For example suitable manipulanda may include one or more physical buttons, sliders, switches, dials, joysticks, trackballs, mice, or keyboards. For example, the base unit 110 may include one or more joystick devices to control the orientation and positioning of the articulating arm 120 or AMF head 122. Further, one or more dials or switches may be employed to select a target temperature, to establish a treatment duration, or to start or stop a treatment session.

The processor 112 executes program code stored in the computer-readable medium 113. The program code provides software that controls the operation of the AMF system 100, including providing one or more user interfaces displayed on the operator display 114, feedback control of the intensity of AMF radiation output by the AMF head based on a sensed temperature of a target, and control of other characteristics of the AMF radiation applied to the target, such as duration and frequency.

The one or more temperature sensors 130 are configured to detect a temperature of a target placed below the AMF head 122 of the articulating arm 120 and to provide sensor signals to the processor 112. In this example, the temperature sensor is mechanically coupled to the articulating arm 120, though in some examples, it may not be mechanically coupled to either the base unit 110 or the articulating arm 120. For example, a temperature sensor may be positioned on the same surface as the target or may be positioned on the target itself. The processor 112 can receive sensor signals from the temperature sensor(s) 130 and control the AC generator and power supply to adjust the AC signal provided to the AMF head 122 to control the amount of AMF radiation projected onto the target. By doing so, the processor may be able to control the temperature of the target.

Figure 8:
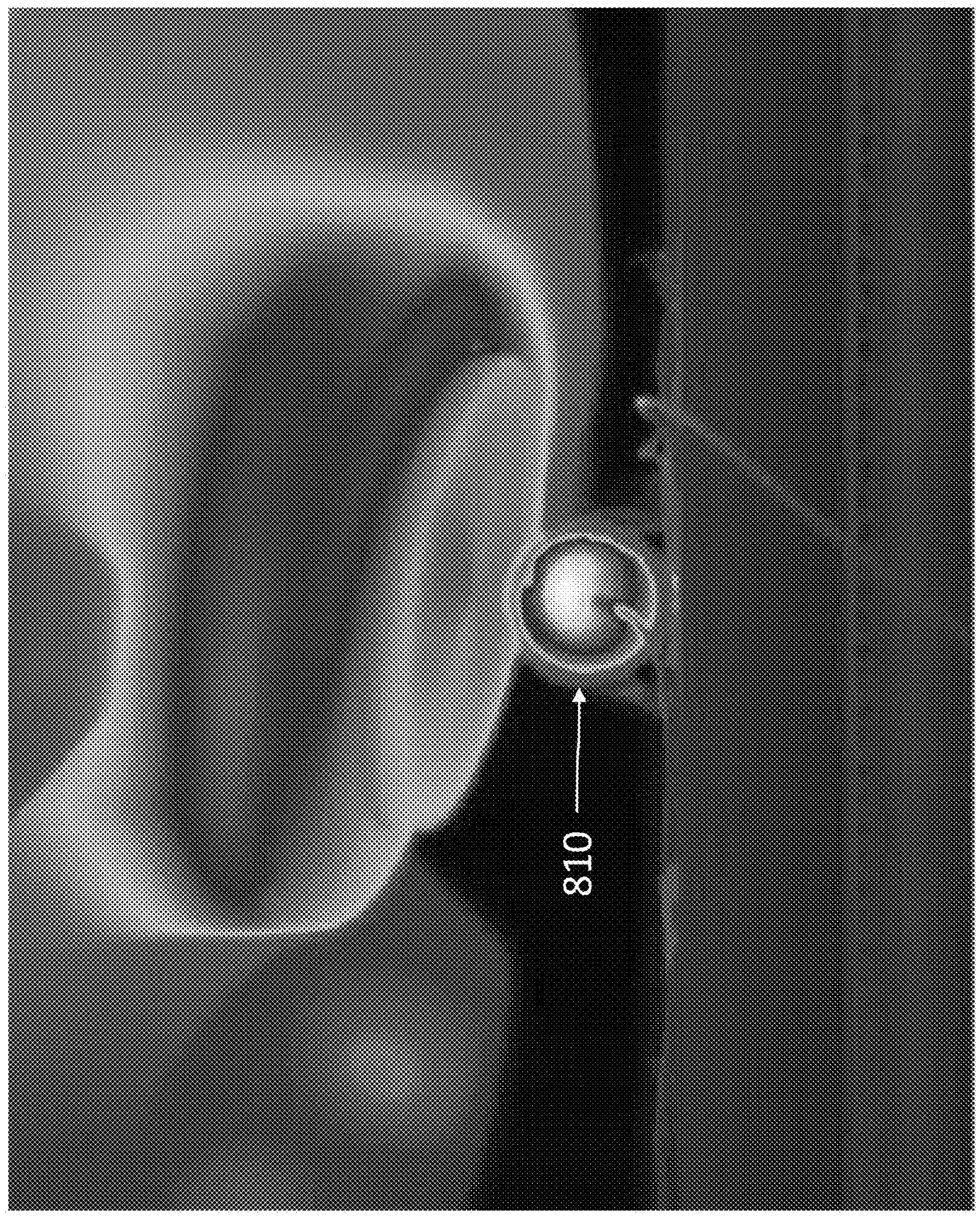
FIG. 8 show an example infrared image of a target.

Example temperature sensors 130 may include contact and non-contact temperature sensors. For example, the temperature sensor 130 may include an infrared (IR) camera configured to capture one or more images of the target, and may also be capable of capturing temperatures beneath the surface of the target. An example image 800 of a target 810 captured by an IR camera is shown in FIG. 8. In some examples the temperature sensor 130 may include a passive non-contact infrared sensor or a suitable contact sensor, such as a non-ferrous thermocouple. In some examples, multiple temperature sensors 130 of the same type or different types may be employed.

The AC signal generator 115 includes a transformer configured to receive an input AC electrical signal from a power source, and to change the voltage, current, or frequency of the input AC electrical signal into the AC generator signal, which is output to the AMF head. In this example, the AC signal generator can output AC signals having frequencies in the range of 80-250 kHz, though in some examples, frequencies in the range of 100-110 kHz may be employed, such as 106 or 109 kHz. A suitable frequency may also be selected based on factors, such as the rate of heating of a particular target, and may be based on a resonant frequency of the target, which will be described in more detail below.

As discussed above, the AMF head 122 includes an electrical coil 122 and a ferromagnetic core 124. The electrical coil 122 includes an electrically-conductive wire wrapped in an approximately cylindrical arrangement around a void to create an approximately cylindrical cavity. The electrical conductor, e.g., a wire, may be wrapped one or more times around the void, with each complete wrapping referred to as a winding. In this example, the electrical coil 122 includes ten windings, though in other examples, different numbers of windings may be used. In some examples, the number of windings can be selected based on a desired resonant frequency for the AC signal provided by the AMF generator to AMF head. As an AC signal is transmitted through the electrical coil, it generates, in conjunction with the core, an AMF that may be projected onto a target. The strength of the AMF is based in part on the magnitude of the AC signal as well as resonance within the AC signal generator 115, the conductors carrying the AC signal to the AMF head, the electrical coil, and the ferromagnetic core. By selecting a number of windings in the electrical coil and the transformer in the AC signal generator, the AMF system may be tuned to output an AMF at a frequency that is resonant to the AMF system 100. Thus, a number of windings in the electrical coil and the transformer of the AC signal generator 115 may be selected to provide resonance at particular frequencies. Providing an AC signal at a resonant frequency may allow for a lower magnitude AC signal to be provided, while still maintaining an AMF of desirable strength, thus enabling the AMF system 100 to more efficiently apply an AMF to the target.

Figures 3A, 3B:
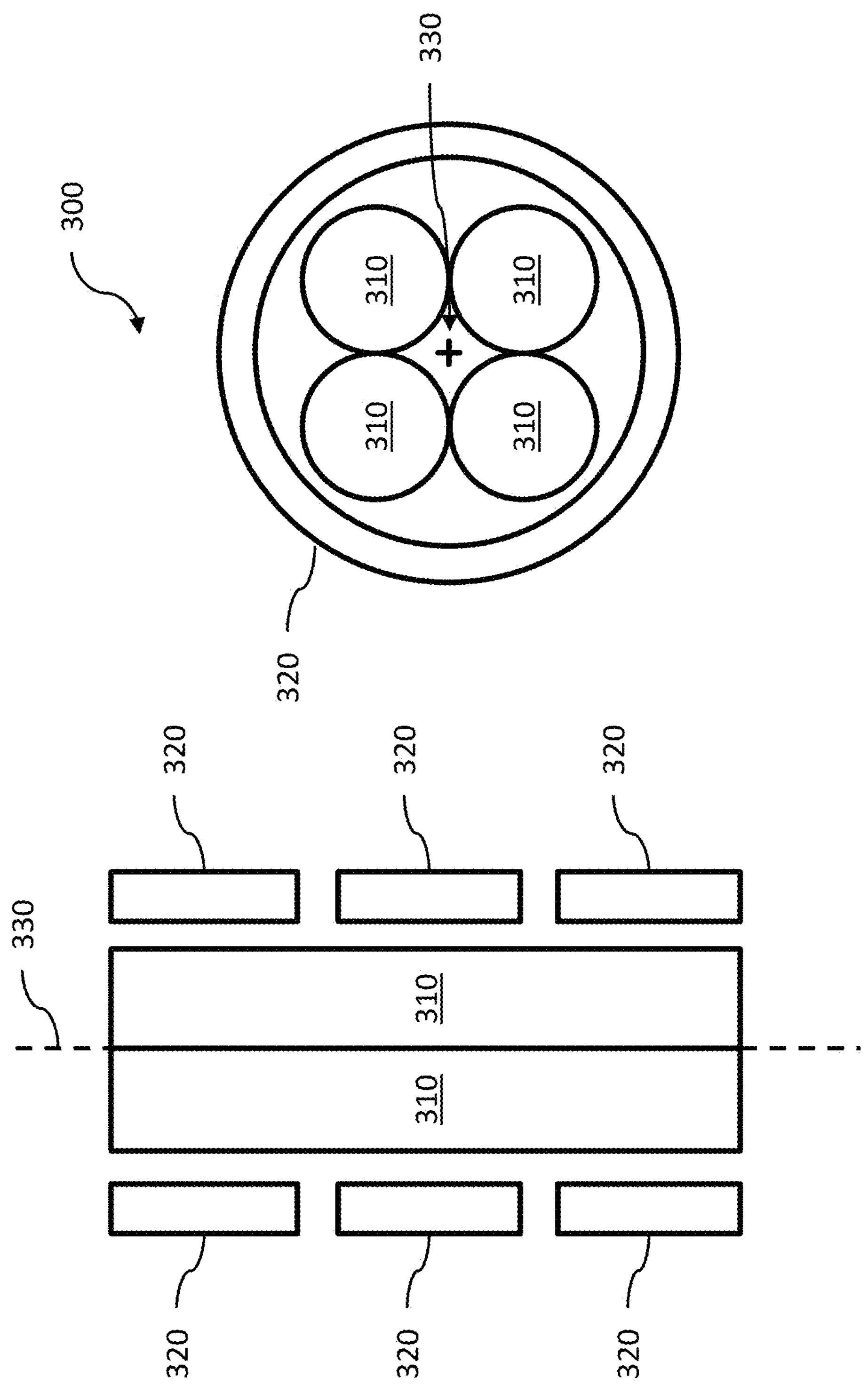
Figure 4B:
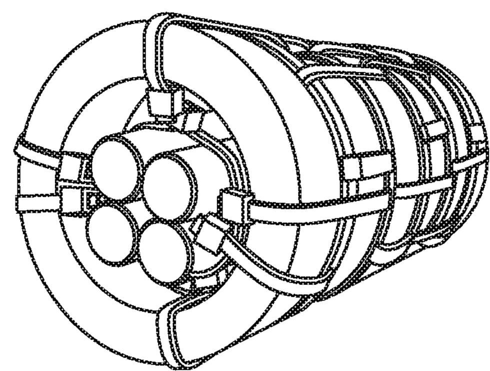
Figure 4A:
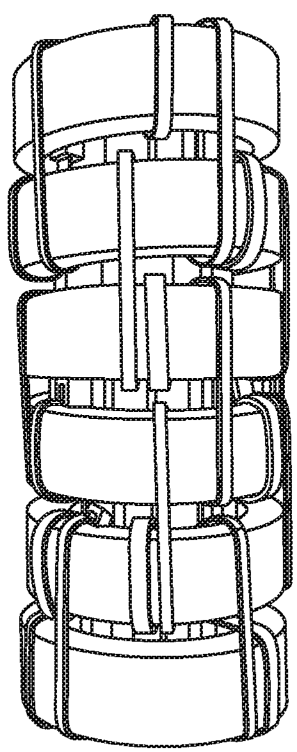

The electrical coil 124 also is sized to accommodate the ferromagnetic core 124 within the cavity defined by the electrical coil. In this example, the ferromagnetic core 124 is approximately 2 inches in diameter and approximately 5 inches tall. In this example, the AMF head 122 includes a ferromagnetic core 300 as shown in FIGS. 3A-3B. FIG. 3A shows a partial cross section in a vertical plane of an example ferromagnetic core 300 suitable for use with some example AMF systems according to this disclosure, while FIG. 3B shows a cross section in a horizontal plane of the example ferromagnetic core 300. It should be noted that the ferromagnetic core 300 of FIGS. 3A-3B is not shown to scale. FIGS. 4A-4B show an additional example of a ferromagnetic core similar to that shown in FIGS. 3A-3B.

The ferromagnetic core 300 includes six exterior ferromagnetic ring elements 320 arranged to form a cavity, in which are inserted four ferromagnetic rods 310, all of which are oriented along a longitudinal axis 330 of the ferromagnetic core 300 running from a first end of the ferromagnetic core 300 to a second end of the ferromagnetic core 300. The ferromagnetic ring elements 320 are arranged such that there is an air gap between adjacent ferromagnetic ring elements 320. The ferromagnetic elements 310, 320 in this example are held in place using one or more plastic elements. Still other non-conductive materials may be employed, including various elastomers and resins, to maintain a shape of a core. The plastic elements may be one or more plastic zip ties or one or more plastic spacers disposed between the ferromagnetic ring elements 320 or the ferromagnetic rods 310, or the ferromagnetic elements 310, 320 may be embedded in a plastic substrate. In some examples, plastic elements disposed between exterior ferromagnetic ring elements 320 may be configured to change in size, such as via a splitter mechanism. In some examples, the material may include one or more inflatable elements that may be inflated or deflated to change a spacing between one or more of the ferromagnetic ring elements 320. In some examples, the sizes of the air gaps may affect a resonant frequency of the AMF head 122 or the AMF system 100, at which the AMF head may more efficiently generate an AMF. Thus, by incorporating such inflatable elements or such mechanical adjustment mechanism within the AMF head 122, the AMF system 100 may adjust its resonant frequency. For example, as will be discussed in more detail, a resonant frequency for a target may be determined, after which time, the resonant frequency of the AMF head or AMF system may be adjusted to more closely match the determined resonant frequency of the target.

In some examples different numbers of ferromagnetic ring elements 320 or ferromagnetic rods 310 may be employed. For example, a suitable ferromagnetic core may include a stack of four ferromagnetic ring elements 320 with six ferromagnetic rods 310 disposed within a cavity defined by the ferromagnetic ring elements 320. In some examples, only one ferromagnetic rod 310 may be employed.

In this example, the ferromagnetic elements 310, 320 are made of a manganese zinc (MnZn) composite material having a permeability of approximately 2,300; however, other suitable materials may be employed as well, such as a nickel zinc (NiZn) material or iron-based materials. Suitable materials may have a permeability within the range from 400 to 10,000, though a permeability as low as 125 may be acceptable.

The electrical coil 124 and ferromagnetic head 126 in this example are positioned within the AMF head 122 such that a longitudinal axis of the electrical coil 124 and ferromagnetic core 126 exits a bottom surface of the AMF head at an orientation orthogonal to the bottom surface. In addition, the first end of the electrical coil 124 and the ferromagnetic head 126 are positioned such that they are substantially flush with the bottom surface of the AMF head 122. It should be noted that in some examples, the electrical coil 124 and ferromagnetic core 126 may not be exposed to a target, but instead may be covered such that a cover over the first end of the electrical coil 124 or the ferromagnetic core 126 is flush with the bottom surface of the AMF head 122 rather than the electrical coil 124 or ferromagnetic core 126 themselves. Further, in some examples, the electrical coil 124 or ferromagnetic core 126 may extend beyond the bottom surface of the AMF head 122 or may not extend fully to the bottom surface of the AMF 122, and thus are not flush with the bottom surface of the AMF head 122. Further, in some examples, the position of the electrical coil 124 or ferromagnetic 126 may be adjustable with respect to the AMF head 122.

Figure 5A:
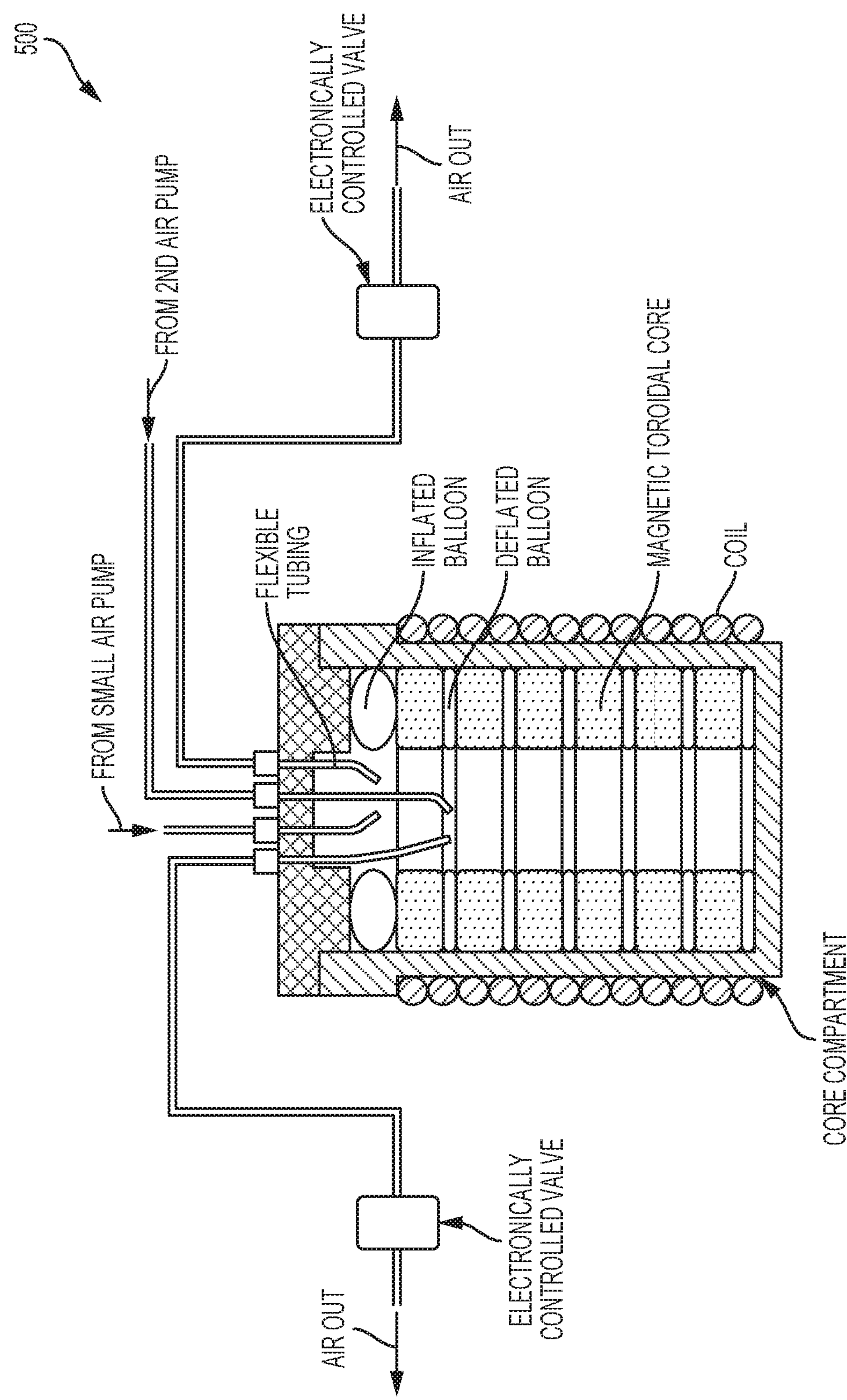
Figure 5B:
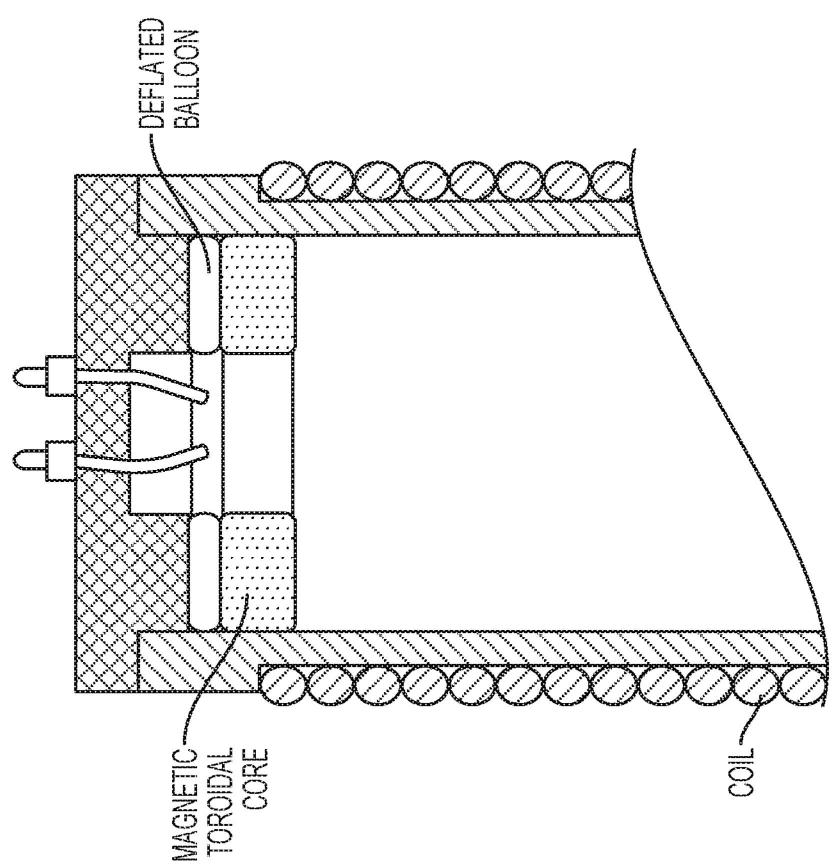

Referring now to FIGS. 5A, FIG. 5B shows a cross-section of an example ferromagnetic core 500 for providing AMF therapy. The example ferromagnetic core 500 shown in this example includes a number of magnetic toroidal core elements stacked vertically within a core compartment. The core compartment is made of a non-ferromagnetic material, such as a plastic material and contains the elements of the core itself. An electrical coil is wound around the exterior of the core compartment. Between one or more of the magnetic toroidal core elements are balloons made of a flexible materials, such as a latex material. Each balloon is connected to an air tube made of a non-ferromagnetic material and fed from an air pump, and each also includes a second air tube connected to an electronically-controlled valve that can be actuated to allow air to escape from the respective balloon. By inserting balloons between core elements, the configuration of the core itself can be changed, such as by inflating or deflating individual balloons. By inflating such elements, spacing between the magnetic toroidal elements can be adjusted, which can change the resonant frequency of the AMF head, thereby allowing for more efficient adjustment of the frequency at which a target is irradiated. By driving the AMF core at a resonant frequency, energy may be more efficiently transferred from the AMF head to the target. Further, as will be discussed in more detail below, if a resonant frequency of a target is known, it may be possible to match the resonant frequency of the AMF head or AMF system to the resonant frequency of the target to more efficiently heat the target.

FIG. 5B shows a second view of the ferromagnetic core of FIG. 5A in which the inflated balloon shown in FIG. 5A is deflated. This example illustrates that the positioning of the magnetic toroidal elements with respect to the coil may be adjusted. For example, if an uppermost or lowermost balloon is inflated or deflated, it can cause the entire ferromagnetic core to move up or down within the coil. Such adjustments may advantageously alter the AMF applied to the target. Thus, the example ferromagnetic core of FIGS. 5A-5B allows for changing of the relative position of individual ferromagnetic core elements, but also the relative position of the ferromagnetic core itself to the coil.

Figure 6:
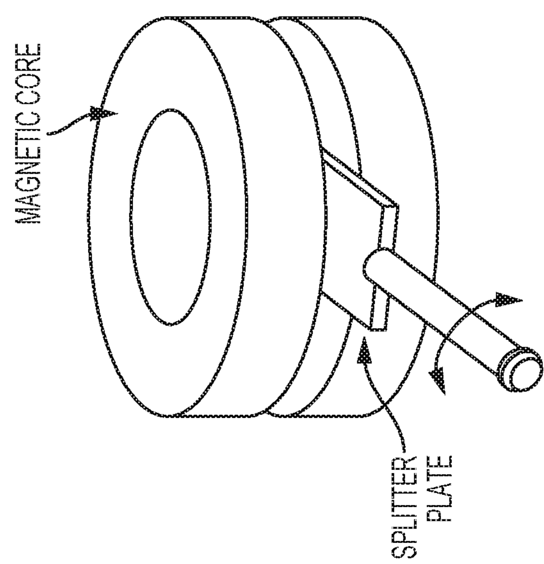

Referring now to FIG. 6, FIG. 6 shows an example ferromagnetic core. In this example, the ferromagnetic core includes individually adjustable core elements, such as the magnetic toroidal elements shown in FIGS. 5A-5B. However, rather than employing balloons, one or more splitter plates may be inserted between individual ferromagnetic core elements. By rotating such splitter plates, the spacing between the ferromagnetic core elements may be adjusted.

Figure 7:
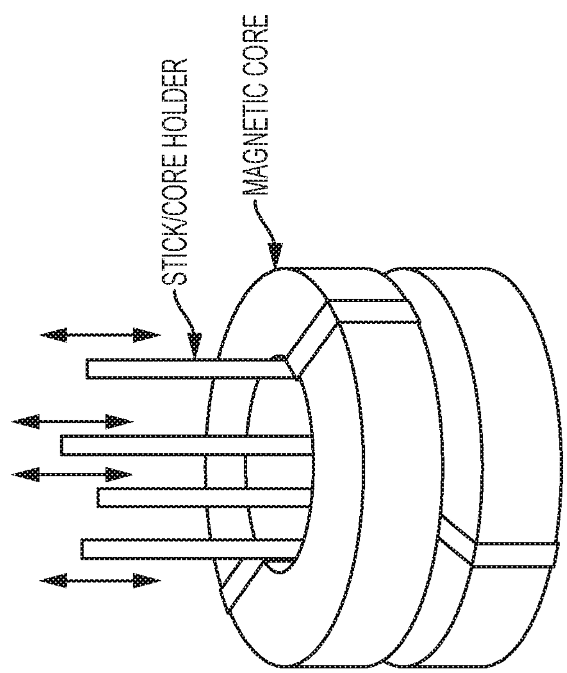

Referring now to FIG. 7, FIG. 7 shows an example ferromagnetic core. In this example, the ferromagnetic core includes individually adjustable core elements, such as the magnetic toroidal elements shown in FIGS. 5A-5B. However, rather than employing balloons or splitter plates, a core element may have a member wrapped around it and attached to a second member that can be pulled or released to raise or lower core elements. For example, one or more strings may be wound around individual core elements and extended upward around a rotatable axle. By rotating the axle, the string may wrap around the axle, drawing the respective core, as well as any cores situated above it, upwards. Similarly, the respective core can be lowered by rotating the axle in the opposite direction. In some examples, rather than string, one or more plastic members, such as zip tie or similar member, having teeth formed on one or more surface may engage with a gear such that rotation of the gear may raise or lower the respective core.

Examples similar to the foregoing may provide an AMF system with tunable AMF characteristics to allow for more efficient generation and application of an AMF.

Figure 9:
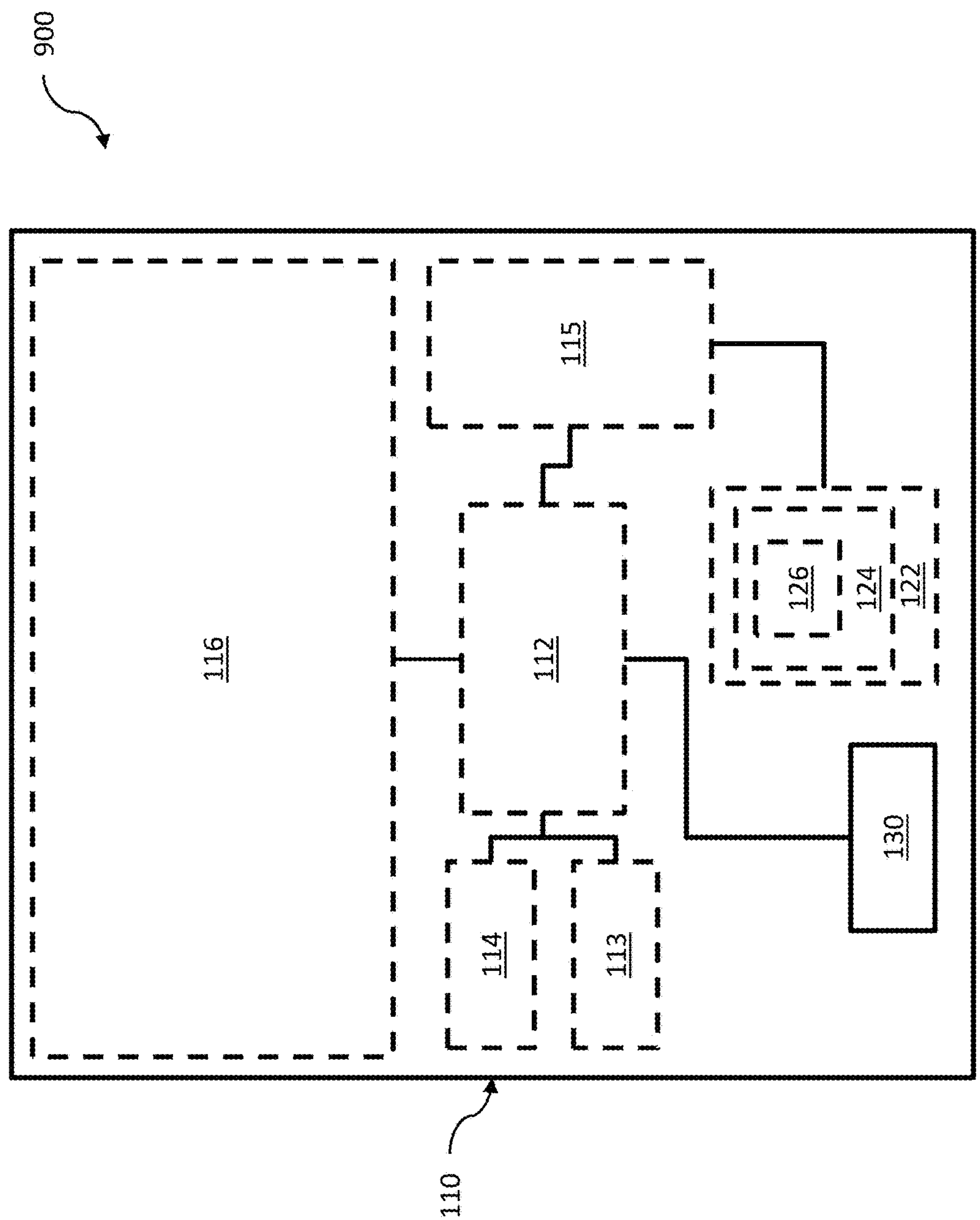
FIG. 9 shows an example system for providing AMF therapy.

Referring now to FIG. 9, FIG. 9 shows an example AMF system 900 that includes the components of the example system of FIGS. 1 and 2A-2J, however, the example AMF system 900 of FIG. 9 lacks an articulating arm. In this example, the AMF system 900 includes an AMF head 122 that is mounted to the base unit and a target may be positioned beneath the AMF head 122. The height of the AMF head 122 with respect to the target may be adjusted, however, otherwise, the position of the AMF head 122 is fixed. Further, in some examples, a plurality of AMF heads 122 may be mounted to the base unit 110 having different orientations, but each directed towards a common location such that a target placed at the common location will receive substantially the same amount of AMF radiation from each of the AMF heads 122. Further, such AMF heads may be positioned such that a patient in a prone position may be able to lay such that the AMF heads 122 partially or fully encircle the patient, thereby allowing the patient to be inserted into the base unit 110, or a portion of the base unit, and receive AMF radiation from one or more of the AMF heads 122.

In some examples, rather than positioning a plurality of AMF heads 122, the electrical coil may be positioned and sized to allow a patient or a part of a patient, such as an arm or leg, to be inserted within the cavity defined by the coil. In some such examples, the AMF system 900 may not include a ferromagnetic core, though in some examples, a core may be positioned within the cavity defined by the electrical coil and may be used to direct AMF onto the target inserted within the cavity.

Figure 10:
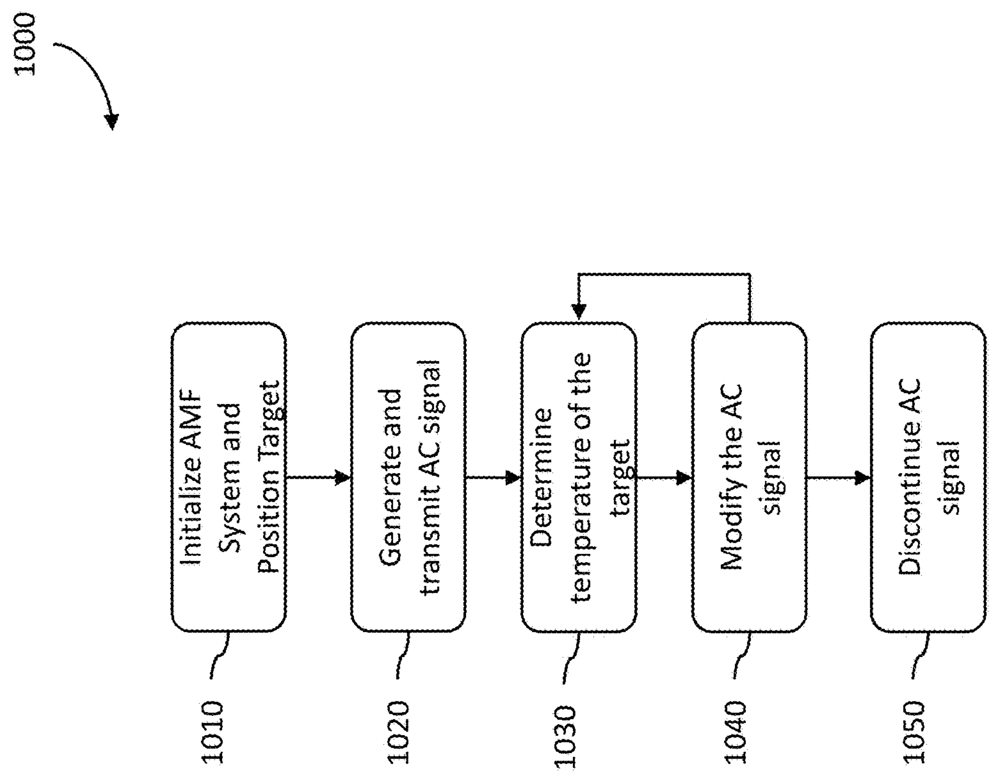
FIG. 10 shows an example method for providing AMF therapy.

Referring now to FIG. 10, FIG. 10 illustrates an example method for providing AMF therapy according to one example. The method of FIG. 10 will be described with respect to the AMF system 100 of FIGS. 1-2J, however, other suitable AMF systems may be employed as well. For example, some example methods according to this disclosure may be performed with respect to the AMF system 900 of FIG. 9.

The method 1000 of FIG. 10 begins at block 1010 when the AMF system 100 is initialized and prepared for applying an AMF to a target. In this example, the AMF system 100 includes an articulating arm 120, which can be maneuvered into proximity with a target. For example, a patient with a tumor in their arm may sit at a table and rest their arm on the table. A location on the patient's arm may be marked to indicate a location of the tumor to allow for easier targeting of the correct area. Further, the tumor has been injected with ferromagnetic nanoparticles, such as MCL nanoparticles.

After the patient is properly situated, the operator of the AMF system 100 then interacts with a graphical user interface (GUI) displayed on the operator display 114 to move the articulating arm 120 and to position the AMF head with respect to the patient's arm and target the location of the tumor. While some examples of the AMF system 100 employ a GUI to control the positioning of the articulating arm 120, in some examples, the operator may use another input device, such as a joystick to maneuver the AMF head 122 into position.

In this example, the operator moves the AMF head 122 to a position above the patient's art such that the target, e.g., the tumor in this case, is positioned beneath the electrical coil 124 and ferromagnetic core 126 such that the longitudinal axis through center of the ferromagnetic core 126 is pointed at the target. The AMF head 122 is positioned such that a first end of the electrical coil 124 or ferromagnetic core 126 is approximately 10 mm from the patients arm, though in some examples the distance between the AMF head 122 and the target may be a greater or lesser distance, such as within the range of 5 to 30 mm. Further, in some examples, the AMF head may be brought into contact with the target, or with a material overlaid on the target, such as a plastic sheet.

After the AMF head has been moved into position, the operator enters the course of treatment into the AMF system 100. For example, the operator enters a desired temperature for the target and a duration over which to maintain the temperature. In some examples, the treatment may vary the temperature over time or may specify a rate of change in the temperature of the target, such as to limit the rate at which the temperature of the target is increased. Such parameters may increase a patient's comfort, e.g., by reducing anxiety about burns, or may provide a more effective course of treatment. Once the course of treatment has been programmed, the operator may instruct the AMF system 100 to begin the treatment, e.g., by pressing a button or entering a command.

At block 1020, the AMF system 100 generates and transmits an alternating current (AC) signal to the AMF head. In this example, after the operator instructs the AMF system 100 to begin a programmed course of treatment, the processor 112 transmits a signal to the AC signal generator 115 to generate an AC signal. In some examples, the processor 112 may transmit multiple signals to the AC signal generator 115, for example to set a frequency for the AC signal and a power level for the AC signal. In response to receiving the one or more signals, the AC signal generator 115 generates and transmits a signal to the AMF head 112. In this example, the AC signal initially comprises a 106 kHz sinusoidal AC signal at approximately 8 kW. In some examples, AC signals may comprise other waveforms, such as square waves or sawtooth waves. In some examples, the power level of the AC signal may be greater than or less than 8 kW, based on a desired rate of heating of a target.

As the AC signal travels through the electrical coil 124, which generates an AMF. The AMF is amplified by the ferromagnetic core 126 and projected onto the target, e.g., the patient's tumor. The AMF interacts with the ferromagnetic nanoparticles, which causes them to heat up, which in turn causes the surrounding tissue to heat up.

Figure 11:
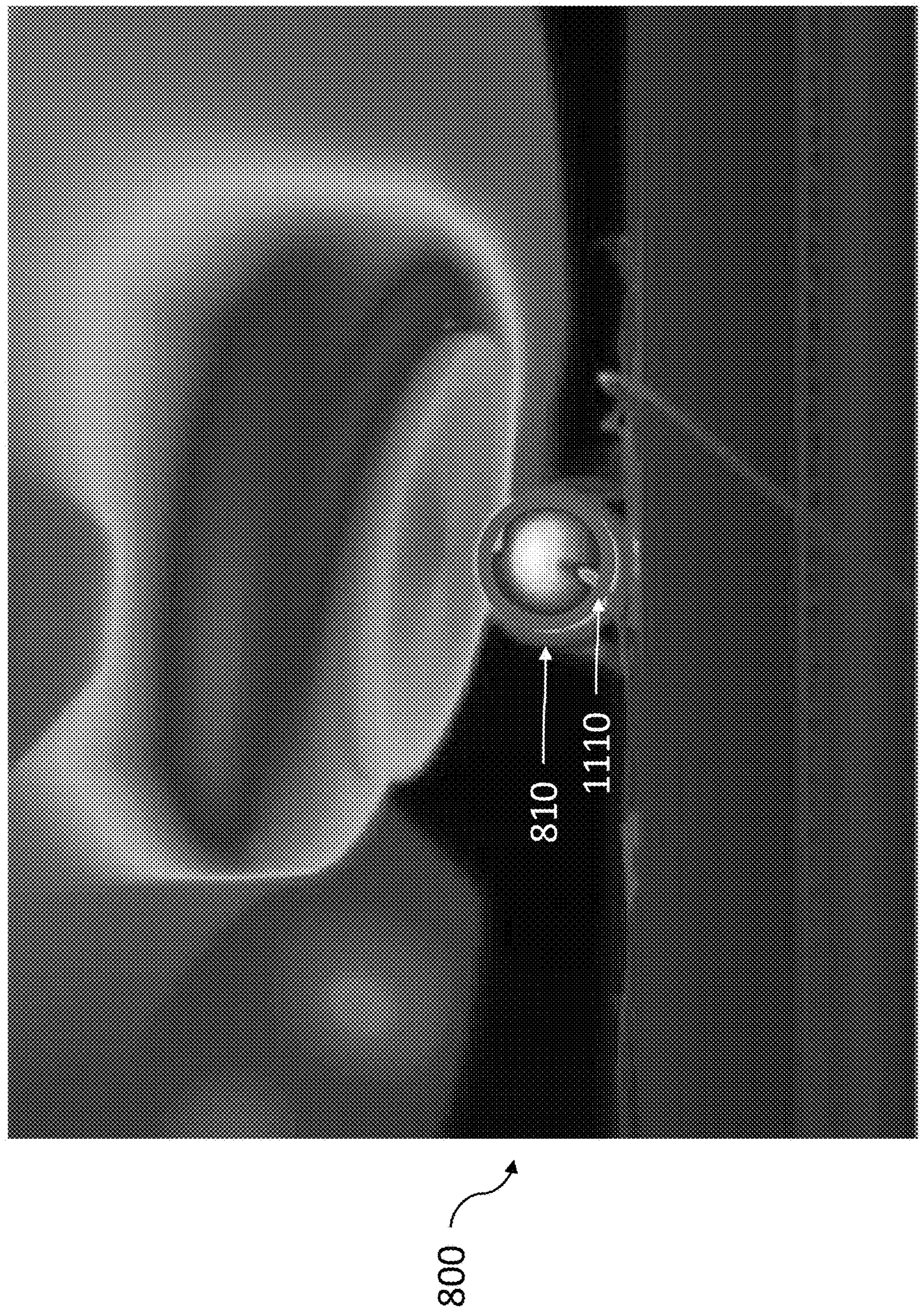
FIG. 11 shows an example infrared image of a target and selection of a region corresponding to the target.

At block 1030, the AMF system 100 determines a temperature of the target based on a sensor signal from a temperature sensor. In this example, the temperature sensor 130 includes an IR camera oriented towards the target. As the AMF system 100 outputs the AMF, the processor 112 receives one or more images from the IR camera at a predetermined rate, such as once per second, to determine a temperature of the target. In this example, the processor 112 provides one or more of the images to the operator display and prompts the operator to identify the portion of the image corresponding to the target. To identify the target within the image, the operator display allows the user to draw a boundary around the target. FIG. 11 shows the IR image 800 of FIG. 8 as well as the target 810 and a boundary 1110 that has been drawn around the target 810 on the operator display 114. Based on the identified target, the processor 112 determines colors of pixels within the identified region, e.g., region 1110, and determines temperatures corresponding to the different colors.

In this example, the AMF system 100 has been configured with a correspondence between different colors and temperatures. For example, red, orange, yellow, and white colors indicate temperatures ranging from 30-50 degrees Celsius, while temperatures between 10 and 30 degrees Celsius are indicated by green, blue and purple colors. In this example, color values for pixels within the bounded region are determined and a maximum and minimum value range is established, and an average temperature is established. The processor 112 then excludes pixels having temperatures more than one standard deviation below the average temperature, and using the remaining pixels determines a second average temperature of the target as well as a maximum temperature of the target. In this example, the processor 112 determines the temperature of the target to be the second average temperature. In some examples, however, the processor 112 determines the maximum temperature of the target in an image to be the temperature of the target. Still other examples may be employed, such as averaging the temperatures associated with all of the pixels within the boundary, or only pixels within half the radius from the center or centroid of the bounded region 710.

At block 1040, the AMF system 100, in response to determining the temperature, modifies the AC signal based on a difference between the temperature and a predetermined target temperature. For example, after the AMF system 100 has projected an AMF onto the patients arm for 60 seconds, the tumor may have increased its temperature to 45 degrees Celsius, while the predetermined target temperature was set by the operator to be 46 degrees. The processor 112 then calculates modifications to the AC signal, such as by calculating a new AC signal or new parameters for the AC signal. In this example, the processor employs a proportional-integral-derivative (PID) control algorithm to determine the AC signal. In some examples, other types of control algorithms may be employed, by eliminating one or more of the P, I, or D portions of the control algorithm.

Figure 12:
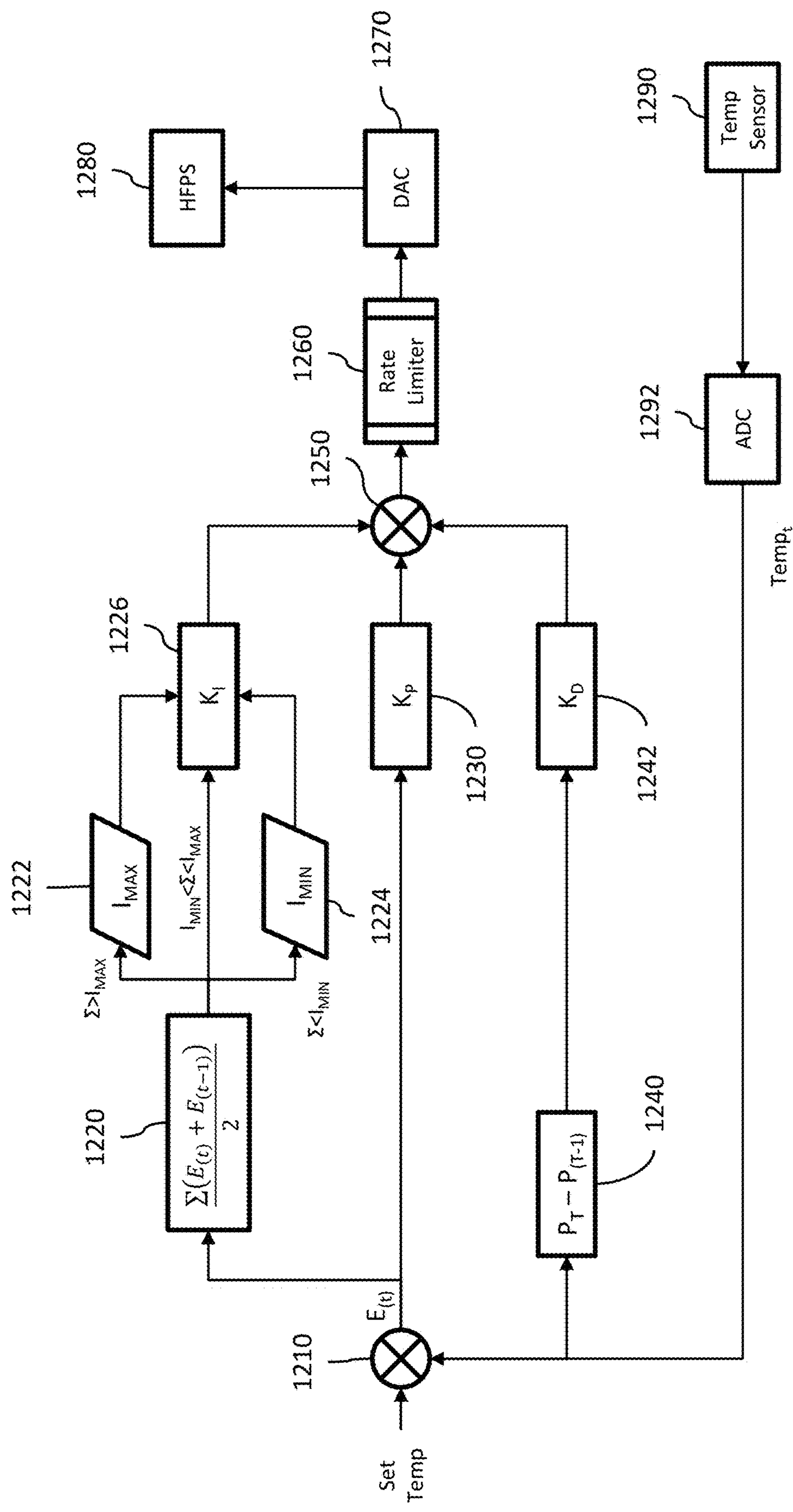
FIG. 12 shows an example control system for providing AMF therapy.

Referring now to FIG. 12, FIG. 12 illustrates an example of a suitable PID control system. In this example, a desired temperature is established by the operator, and a current detected temperature is provided by the temperature sensor 1290 via an analog to digital converter (ADC) 1292. The desired temperature is compared to the detected temperature at block 1210 to determine the current temperature difference at time, t, to establish the current error, $E_{(t)}$. The error is fed into the integral controller 1220, where the current error and the last calculated error are averaged and added to the then-current integral state to obtain a new integral control state. If the new integral control state is greater than the maximum integral control state ($I_{MAX}$), or less than the minimum integral control state ($I_{MIN}$), the new integral control state is set to either $I_{MAX}$ at block 1222 or $I_{MIN}$ at block 1224. The new integral control state is then multiplied by the integral coefficient, $K_I$, at block 1226 to determine the integral term for the PID controller.

The proportional term is computed by multiplying the current error, $E_{(t)}$, with the proportional coefficient at block 1230.

The derivative term is computed from the difference between the prior derivative state and the current temperature at block 1240, and the difference is multiplied by the differential coefficient, $K_D$, at block 1242.

In this example, the coefficients ($K_I$, $K_D$, and $K_P$) are set such that $K_I$=1.5, $K_P$=25, and $K_D$=0; however, other coefficients may be selected based on design parameters, such as allowable temperature overshoot and a desired ramp time. For example, a maximum allowable temperature overshoot may be established at 50 degrees Celsius, which may relate to a temperature at which human tissue begins to die from excess heat. Further, in this example, the values for $I_{MAX}$ and $I_{MIN}$ have been set to $I_{MAX}$=300 and $I_{MIN}$=100.

Example source code for providing a PID control system is also provided in Appendix A to this specification.

A new drive signal for the high-frequency power supply (HPFS) 1280 is computed by summing the integral term, the proportional term, and the derivative term. The new drive signal is sent to a rate limiter 1260, which adjusts the signal based on a limit on the rate at which the drive signal for the HPFS can be changed, e.g., no more than 25% increase or decrease per second. For example, if the new drive signal received by the rate limiter represents a 50% increase in magnitude over the previous drive signal, the rate limiter only increases the magnitude of the drive signal by 25%. After making any adjustments to the drive signal based on the maximum rate of increase or decrease, the rate limiter 1260 outputs the new drive signal to a digital to analog converter (DAC) 1270, which generates an analog drive signal to drive the HFPS at block 1280.

After modifying the AC signal, the method returns to block 630 unless the course of treatment is completed, at which time the method proceeds to block 650 at which time the AMF system 100 discontinues the AMF by discontinuing the AC signal.

Figure 13:
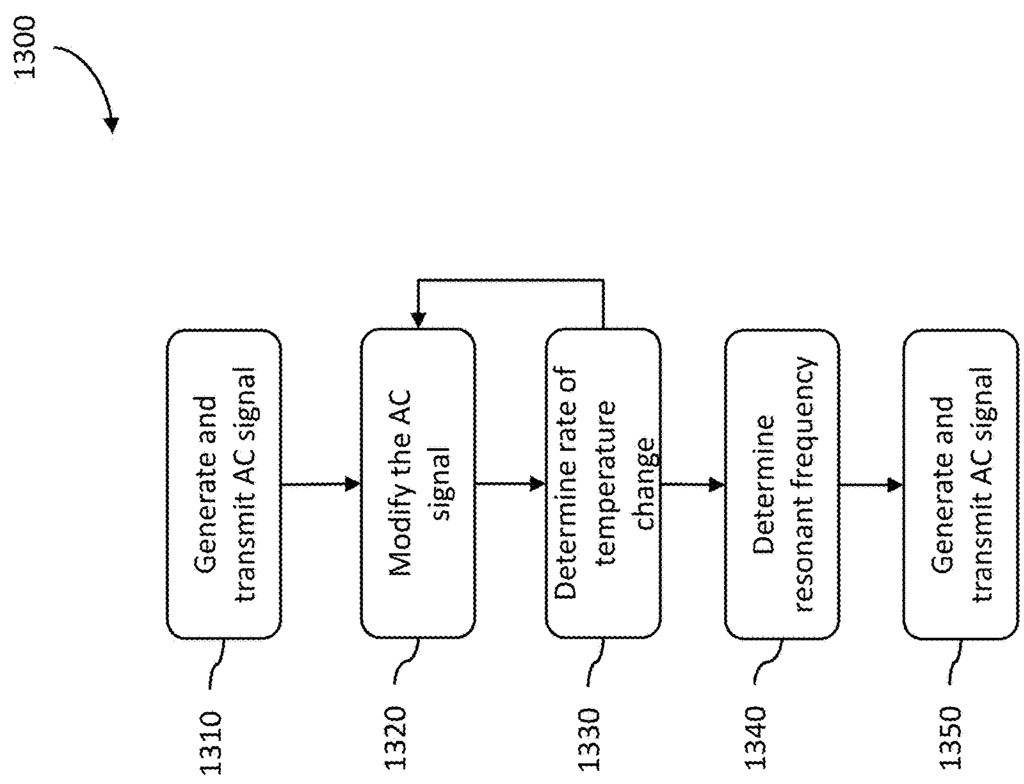
FIG. 13 shows an example method for providing AMF therapy.

Referring now to FIG. 13, FIG. 13 illustrates an example method for providing AMF therapy. The example method 1300 shown in FIG. 13 determines a resonant frequency of a target and may be employed to more efficiently increase or maintain a desired temperature of the target. For purposes of this example, the method 1300 is performed by the example AMF system 100 of FIG. 1. Further, the example method 1300 is described in the context of a target that has already been heated to a desired temperature and the AMF system 100 is maintaining the temperature for a predefined duration. However, in other examples, the method 1300 may be started prior to reaching a desired temperature.

At block 1310, the AMF system 100 generates and transmits an alternating current (AC) signal to the AMF head as described above with respect to block 620 of the method 600 of FIG. 6.

At block 1320, the processor 112 modifies the AC signal. In this example, the processor 112 increases the frequency of the AC signal by 1 kHz and increases the power by 1 kW to induce heating; however, in other examples, the processor 112 increases the frequency of the AC signal by a smaller or larger amount, such as by 500 Hz or 2 kHz. In some examples the processor 112 may also decrease a frequency of the AC signal. For example, after a certain number of iterations, the processor may return to the initial frequency and then begin reducing the frequency in steps. In some examples, the size of a change in the frequency may decrease over time as the processor hones in on a possible resonant frequency of the target.

At block 1330, the processor 112 determines a rate of change of temperature of the target at the then-current frequency. For example, the processor 112 may maintain the new frequency for a period of two seconds and measure the change in temperature after the two seconds has elapsed. The processor 112 may then determine the rate of change by subtracting the starting temperature from the ending temperature and dividing by the elapsed time. After determining the rate of temperature change, the processor 112 allows the target to return to the desired temperature and then the method returns to block 1320 to evaluate a new frequency. The method may proceed to block 1340 after a predetermined frequency range has been attempted. For example, the AMF system 100 may initially employ a 106 kHz AC signal to bring the target up to a desired temperature. The AMF system 100 may then attempt to search a frequency range between 100-120 kHz.

At block 1340, the AMF system 100 determines a resonant frequency of the target. In this example, the AMF system 100 identifies a frequency within the range of frequencies tested at blocks 1320 and 1330 to identify the frequency corresponding to the highest rate of temperature change to identify the resonant frequency of the target. In some examples, the identified frequency may not be a true resonant frequency of the target, but instead may represent a frequency that results in a more efficient heating of the target.

At block 1350, the AMF system 100 generates and transmits the AC signal at the determined resonant frequency. Such a frequency may enable the AMF system 100 to maintain a temperature of the target at a reduced power setting for the AC signal generator, i.e., an AMF at the determined resonant frequency may more efficiently transfer energy to the target than the initially-selected frequency. The AMF system 100 may then continue with the course of treatment for the remainder of the established treatment duration.

While some examples of methods and systems herein are described in terms of software executing on various machines, the methods and systems may also be implemented as specifically-configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs for editing an image. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes all of the following alternative combinations as appropriate for a particular usage: A alone; B alone; C alone; A and B only; A and C only; B and C only; and A and B and C.

That which is claimed is:

1. A system comprising:

an alternating magnetic field (AMF) head, the AMF head comprising an electrical coil and a ferromagnetic core, the electrical coil having a plurality of windings defining an interior region, the ferromagnetic core at least partially disposed within interior region defined by the electrical coil, the AMF head having a first end corresponding to a first end of the electrical coil and a second end corresponding to a second end of the electrical coil;

an AMF generator coupled to the AMF head, the AMF generator configured to generate an alternating current (AC) signal and transmit the AC signal to the electrical coil of the AMF head;

a temperature sensor configured to sense a temperature of a target positioned proximate to the first end of the AMF head, the temperature sensor positioned external to a patient's body and comprises an infrared sensor, an infrared camera, or a visible light camera; and a processor in communication with the AMF generator and the temperature sensor, the processor configured to: iteratively:

detect a rate of change of temperature of the target at a first frequency, store the rate of change of temperature associated with th first frequency, change the frequency to a second frequency, detect a rate of change of temperature of the target at the second frequency, and store the rate of change of temperature associated with the second frequency;

determine a resonant frequency of the target based on the stored rates of change of temperature; and generate and transmit a control signal to the AMF generator based on the resonant frequency, the control signal configured to cause the AMF generator to output the AC signal with a first magnitude or at a first frequency to project an AMF onto the target, receive a sensor signal from the temperature sensor, the sensor signal indicating the temperature of the target, modify the control signal to cause the AMF generator to change the first magnitude to a second magnitude, or to change the first frequency to a second frequency, based on a difference between the sensed temperature and a predetermined target temperature, and transmit the modified control signal to the AMF generator to project a modified AMF onto the target.

2. The system of claim 1, wherein the first frequency comprises a resonant frequency of the AMF head.

3. The system of claim 1, wherein the second frequency comprises a resonant frequency of the AMF head.

4. The system of claim 1, wherein the predetermined target temperature is between 43-48 degrees Celsius.

5. The system of claim 1, wherein the AMF head comprises a resonant frequency, and wherein the processor is further configured to transmit a signal to change a configuration of the ferromagnetic core, and wherein the resonant frequency of the AMF head varies based on the configuration of the ferromagnetic core.

6. The system of claim 5, wherein the AMF head further comprises an inflatable member coupled to the ferromagnetic core, and wherein the signal causes the inflatable member to change a level of inflation to change the configuration of the ferromagnetic core.

7. The system of claim 5, wherein the AMF head further comprises a separating member coupled to the ferromagnetic core, the separating member configured to increase or decrease a spacing between at least two components of the ferromagnetic core, and wherein the signal is configured to cause the separating member to increase or decrease the spacing between at least two of the at least two components of the ferromagnetic core.

8. The system of claim 1, wherein the processor is further configured to transmit a signal to change a configuration of the ferromagnetic core based on the resonant frequency of the target.

9. The system of claim 1, wherein the processor is further configured to generate and transmit the AC signal to the AMF head at the resonant frequency of the target.

10. A method comprising:

positioning a target proximate to a first end of an alternating magnetic field (AMF) head, the AMF head comprising an electrical coil and a ferromagnetic core, the electrical coil having a plurality of windings defining an interior region, the ferromagnetic core at least partially disposed within interior region defined by the electrical coil, the AMF head having the first end corresponding to a first end of the electrical coil and a second end corresponding to a second end of the electrical coil;

iteratively:

detecting a rate of change of temperature of the target at a first frequency, storing the rate of change of temperature associated with the first frequency, changing the frequency to a second frequency, storing the rate of change of temperature associated with the second frequency, determining a resonant frequency of the target based on the stored rates of change of temperature;

generating and transmitting an alternating current (AC) signal to the AMF head to project an AMF onto the target based on the resonant frequency;

determining a temperature of the target based on a sensor signal from a temperature sensor, the temperature sensor positioned external to a patient's body and comprises an infrared sensor, an infrared camera, or a visible light camera; and in response to determining the temperature, modifying the AC signal based on a difference between the temperature of the target and a predetermined target temperature to project a modified AMF onto the target.

11. The method of claim 10, wherein the AMF head comprises a resonant frequency, and further comprising changing a configuration of the ferromagnetic core, and wherein the resonant frequency of the AMF head varies based on the configuration of the ferromagnetic core.

12. The method of claim 11, wherein the AMF head further comprises an inflatable member coupled to the ferromagnetic core, and further comprising changing a level of inflating an inflatable member to change the configuration of the ferromagnetic core.

13. The method of claim 11, wherein the AMF comprises a separating member coupled to the ferromagnetic core, the separating member configured to increase or decrease a spacing between at least two components of the ferromagnetic core, and further comprising causing the separating member to increase or decrease the spacing between at least two of the at least two components of the ferromagnetic core.

14. The method of claim 10, further comprising changing a configuration of ferromagnetic core based on the resonant frequency of the target.

15. The method of claim 10, further comprising generating and transmitting the AC signal to the AMF head at the resonant frequency of the target.

16. The method of claim 10, wherein the AC signal has a first frequency, and the first frequency comprises a resonant frequency of the AMF head.

17. The method of claim 10, wherein the modified AC signal has a second frequency, and the second frequency comprises a resonant frequency of the AMF head.

18. The method of claim 10, wherein the predetermined target temperature is between 43-48 degrees Celsius.

* * * * *